United States Patent
Martin et al.

(10) Patent No.: US 9,822,040 B1
(45) Date of Patent: Nov. 21, 2017

(54) PRESSURELESS SINTERING-BASED METHOD FOR MAKING A TWO-PHASE CERAMIC COMPOSITE BODY

(75) Inventors: Curtis A. Martin, Damascus, MD (US); James A. Zaykoski, Mount Airy, MD (US); Inna G. Talmy, North Potomac, MD (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 800 days.

(21) Appl. No.: 12/287,161

(22) Filed: Oct. 6, 2008

Related U.S. Application Data

(60) Provisional application No. 60/998,459, filed on Oct. 5, 2007.

(51) Int. Cl.
*C04B 35/10* (2006.01)
*C04B 35/58* (2006.01)

(52) U.S. Cl.
CPC .............................. *C04B 35/5805* (2013.01)

(58) Field of Classification Search
CPC .......... C04B 35/5805–35/58078; C04B 35/10; C04B 2235/3808
USPC ......................................... 264/646, 647, 681
See application file for complete search history.

(56) References Cited

U.S. PATENT DOCUMENTS

| | | | |
|---|---|---|---|
| 4,248,814 A * | 2/1981 | Yajima et al. | 264/624 |
| 4,336,215 A * | 6/1982 | Yajima et al. | 264/624 |
| 4,705,761 A * | 11/1987 | Kosugi | 501/87 |
| 4,774,210 A | 9/1988 | Ray | |
| 5,034,355 A * | 7/1991 | Tani et al. | 501/92 |
| 5,342,564 A * | 8/1994 | Wei et al. | 264/656 |
| 5,604,165 A * | 2/1997 | Talmy et al. | 501/96.1 |
| 6,641,640 B1 * | 11/2003 | Hesse et al. | 75/236 |
| 9,399,600 B2 | 7/2016 | Smith et al. | |
| 2005/0143251 A1 * | 6/2005 | Mehrotra et al. | 501/95.3 |
| 2014/0271321 A1 | 9/2014 | Maderud et al. | |

OTHER PUBLICATIONS

Rahaman, M. N.. Ceramic Pricessing and Sintering. New York: Marcel Dekker, Inc, 1995. pp. 637-642.*
W. Acchar, P. Greil, A. E. Martinelli, C. A. A. Cairo, A. H. A. Bressiani, J. C. Bressiani, "Sintering behaviour of alumina-niobium carbide composites", Journal of the European Ceramic Society, vol. 20, Issue 11, Oct. 2000, pp. 1765-1769.*
Postrach, Stefan et al. (2000). Pressureless Sintering of Al2O3 Containing up to 20 vol% Zirconium Diboride (ZrB2). J of the European Ceram Soc, vol. 20, 1459-1468.*
W. D. Kingery, Introduction to Ceramics, John Wiley & Sons, Inc., New York, 1960, p. 622.
William G. Fahrenholtz and Gregory E. Hilmas, "Refractory Diborides of Zirconium and Hafnium," Journal of the American Ceramic Society, vol. 90, No. 5, pp. 1347-1364 (May 2007).
Sumin Zhu, William G. Fahrenholtz, Gregory E. Hilmas, Shi C. Zhang, Edward J. Yadlowsky, and Michael D. Keitz, "Microwave Sintering of a ZrB2—B4C Particulate Ceramic Composite," Composites, Part A, Applied Science and Manufacturing, pp. 449-453 (Mar. 2008).
Sumin Zhu, "Densification, Microstructure, and Mechanical Properties of Zirconium Diboride Based Ultra-High Temperature Ceramics," Doctoral Dissertations, Paper 1985, Missouri University of Science and Technology, 194 pages (Fall 2008).
William G. Fahrenholtz, Gregory E. Hilmas, Shi C. Zhang, and Sumin Zhu, "Pressureless Sintering of Zirconium Diboride: Particle Size and Additive Effects," Journal of the American Ceramic Society, vol. 91, No. 5, pp. 1398-1404 (Apr. 2008).

\* cited by examiner

*Primary Examiner* — Erin Snelting
(74) *Attorney, Agent, or Firm* — Howard Kaiser

(57) ABSTRACT

Inventive manufacture of $CrB_2$—$Al_2O_3$ composites is based on pressureless sintering. According to typical inventive practice, $CrB_2$ powder and $Al_2O_3$ powder are mixed together in selected volumetric proportions so that the volume of the $CrB_2$ does not exceed 50% of the overall volume of the $CrB_2$—$Al_2O_3$ mixture. The $CrB_2$—$Al_2O_3$ mixture is shaped into a green body. The green body is pressureless sintered in a non-oxidizing atmosphere at a firing temperature in the approximate range between 1600° C. and 2050° C. The present invention succeeds in preparing, via pressureless sintering, a proportionality-associated range of compositions in the $CrB_2$—$Al_2O_3$ system, which is a potentially "advanced" ceramic system. A typical inventively fabricated $CrB_2$—$Al_2O_3$ composite is inventively configured in a complex shape, and has "advanced" material (e.g., mechanical) properties that are favorable for a contemplated application. Inventive manufacture of ceramic-ceramic composites is thus dually attributed, and uncommonly so, with complex shape-ability and advanced capability.

15 Claims, No Drawings

PRESSURELESS SINTERING-BASED METHOD FOR MAKING A TWO-PHASE CERAMIC COMPOSITE BODY

CROSS-REFERENCE TO RELATED APPLICATIONS

This application claims the benefit of U.S. provisional patent application No. 60/998,459, hereby incorporated herein by reference, filing date 5 Oct. 2007, invention title "Ballistic Armor Methods, Systems and Materials," joint inventors Curtis A. Martin, Gilbert F. Lee, Jeffrey J. Fedderly, David E. Johnson, David P. Owen, Rodney O. Peterson, Philip J. Dudt, James A. Zaykoski, Inna G. Talmy.

BACKGROUND OF THE INVENTION

The present invention relates to ceramic materials, more particularly to ceramic-ceramic composite materials and methods of making same.

Ceramic materials have seen a variety of applications, including ballistic armor devices, engine parts/components, roller bearings, semiconductors, superconductors, electrical insulators, heat shields, bricks/tiles, orthopedic implants, dental implants, pottery, hot beverage cups/mugs, and statues/figurines/ornaments.

Ceramic materials may be divided into two general groups: oxide ceramics and non-oxide ceramics. The oxides include materials such as aluminum oxide, and are easily prepared by pressureless sintering. The non-oxides, for example tungsten carbide and titanium diboride, have generally higher temperature capability and advanced mechanical properties. These ceramic materials of advanced capabilities (such as involving high toughness or high hardness)—which are in the non-oxide ceramics group—are commonly prepared by pressure-assisted sintering (e.g., hot-pressing), a technique that is not suitable for preparation of an article of complex shape. To the extent that pressureless sintering has been practiced to prepare advanced ceramic materials, this has usually involved the use of a metal sintering aid, which has inevitably resulted in the metal becoming a constituent of the prepared composition and hence altering its properties vis-à-vis the ceramic sans metal. In general, pressure-assisted sintering is limited in terms of reduced production capacity and higher production cost. The need exists in various ceramic-related arts for ceramic materials that are practical and economical for extensive manufacture.

Ballistic armor systems incorporating ceramic material have been used by the military and law enforcement to protect people, stationary structures, and vehicles. Ceramic materials that are especially known to be suitable for ballistic armor applications include aluminum oxide (commonly called "alumina"), silicon carbide, boron carbide, and titanium carbide. These conventional armor ceramics have been developed over the last thirty years or so, represent the current state of the art, and have been relied upon in conventional practice of armor systems—for instance, for protection against impact by a projectile such as a ballistic body (e.g., small arms fire) or an explosive fragment (e.g., shrapnel from a bomb blast).

Conventional ceramic armor materials sometimes fail, or perform less than optimally, when impacted by a projectile. Investigation is continuing in the armor-related arts to improve the capabilities of materials to withstand significant impacts. Furthermore, conventional ceramic armor materials, and armor systems implementing them, tend to be expensive to produce because of the above-noted predominance of pressure-assisted sintering in their preparation.

A "composite" is conventionally understood to mean, in a general sense, a solid whole material composed of at least two solid constituent materials that have different physical characteristics; in the context of the whole material, the constituent materials retain their respective identities and contribute respective properties to the whole material. The terms "two-phase ceramic composite" and "ceramic-ceramic composite" synonymously refer to a composite composed of two different constituent materials that are both ceramic materials. The term "plural-phase ceramic composite" can aptly be applied to a composite composed of two or more different constituent materials each of which is a ceramic material.

Certain two-phase ceramic composites have been demonstrated in testing to have material properties (such as toughness and hardness) that are desirable for armor applications and other applications in which the capability of a material to withstand energy or force is important. See Inna G. Talmy, J. A. Zaykoski, and E. J. Wuchina, "Ceramics in the CrB2-Al2O3 System," *Ceramic Transactions*, volume 74, pages 261-272 (1996), incorporated herein by reference. See also Gary A. Gilde, J. W. Adams, M Burkins, M. Motyka, P. J. Patel, E. Chin, M. Sutaria, M. J. Rigali, and L. P. Franks, "Processing Aluminum Oxide/Titanium Diboride Composites for Penetration Resistance," *Ceramic Engineering and Science Proceedings*, volume 22, number 3, pages 331-342 (2001), incorporated herein by reference.

Talmy et al. demonstrated that a two-phase composite ceramic material composition consisting of chromium diboride ($CrB_2$) and aluminum oxide ($Al_2O_3$) possesses enhanced mechanical properties, as compared with mechanical properties of chromium diboride alone or of aluminum oxide alone. Talmy et al. found an increase in toughness and hardness in various "intermediate" compositions of chromium diboride-aluminum oxide, as compared with pure aluminum oxide or pure chromium diboride. Gilde et al. demonstrated that a two-phase composite ceramic material composition consisting of titanium diboride ($TiB_2$) and aluminum oxide can exhibit enhanced ballistic resistance, especially in terms of penetration resistance, as compared with ballistic resistance exhibited by aluminum oxide alone.

Talmy et al. state on page 263 in their "RESULTS AND DISCUSSION" section: "The optimum hot pressing temperature was 1900° C. for pure $CrB_2$, 1700° C. for $Al_2O_3$ and 1800° C. for all the intermediate compositions. Hot-pressed pure $CrB_2$ ceramics exhibited a coarse-grained structure with some closed porosity located both inside the grains and at grain boundaries (Figure 1(a)). Variations in pressing temperature and time did not eliminate porosity. The relative density of $CrB_2$ did not exceed 94%. However, the porosity was significantly decreased by the addition of just 10 mole % (17 vol. %) of $Al_2O_3$. The relative density of all materials of intermediate composition increased to 98%. The microstructure of these materials was very uniform." Talmy et al. state on page 226 in their "SUMMARY" section: "The densification, microstructure, and properties of ceramics in the $CrB_2/Al_2O_3$ were characterized. The optimum hot pressing temperature was 1900° C. for pure $CrB_2$, 1700° C. for $Al_2O_3$ and 1800° C. for all the intermediate compositions. Hot-pressed pure $CrB_2$ ceramics exhibited a coarse-grained structure with some closed porosity located both inside the grains and at the grain boundaries. The porosity was eliminated by the addition of just 10 mole % of $Al_2O_3$."

The term "toughness" conventionally refers to the ability of a material to absorb mechanical energy without breaking, e.g., to deform plastically before fracturing. Toughness involves both strength and ductility. The term "hardness" conventionally refers to the ability of a material to resist change (e.g., scratching or indentation) under mechanical force.

SUMMARY OF THE INVENTION

In view of the foregoing, an object of the present invention is to provide a technologically and economically feasible methodology for large-scale manufacture of ceramic material bodies having desirable characteristics and complex shapes. Another object of the present invention is to provide such a methodology in which the ceramic material bodies are suitable especially for ballistic armor applications.

The present invention is typically embodied as a method for making a chromium diboride—aluminum oxide two-phase ceramic composite body. The inventive method typically comprises mixing chromium diboride powder and aluminum oxide powder to produce a mixture, shaping the mixture to form a green body, and pressureless sintering the green body in a non-oxidizing atmosphere. The chromium diboride constitutes no more than fifty percent by volume of the mixture, and the aluminum oxide constitutes at least fifty percent by volume of the mixture. The pressureless sintering of the green body is performed in a non-oxidizing atmosphere at a firing temperature in the range between approximately 1600° C. and approximately 2050° C.

According to typical inventive practice, a $CrB_2$—$Al_2O_3$ two-phase composite body is made so as to consist of $CrB_2$ and $Al_2O_3$ in selected volumetric proportions falling within a range. The inventively made $CrB_2$—$Al_2O_3$ two-phase composite body consists of: $CrB_2$ in the range between >0% and 50% of the overall volume of the inventively made $CrB_2$—$Al_2O_3$ two-phase composite body; and, $Al_2O_3$ in the range between 50% and <100% of the overall volume of the inventively made $CrB_2$—$Al_2O_3$ two-phase composite body. According to frequent inventive practice, the chromium diboride constitutes a percentage of the overall volume in the range between approximately 20% and approximately 30%, and the aluminum oxide constitutes a percentage of the overall volume in the range between approximately 70% and approximately 80%. Primarily through selection of the volumetric proportions of the $CrB_2$ constituent and the $Al_2O_3$ constituent, the inventive practitioner can select specific material attributes for specific applications, such as high toughness and/or high hardness for certain armor applications.

Both Talmy et al. and Gilde et al. disclose the making of their respective ceramic-ceramic composite materials via hot pressing, which is a type of pressure-assisted sintering. In general, the necessity to prepare a composition by pressure-assisted sintering represents a significant drawback of that composition, as its practical application is limited due to reduced production capacities and higher production costs. The chromium diboride-aluminum oxide composition disclosed by Talmy et al. is somewhat advantageous vis-à-vis the titanium diboride-aluminum oxide composition disclosed by Gilde et al., insofar as the hot pressing temperature is lower due to the relatively limited solid solubility in a chromium diboride-aluminum oxide system. Notwithstanding possible cost-saving benefit associated with lower hot pressing temperature, because pressure-assisted sintering is inherently limited neither Talmy's $CrB_2$—$Al_2O_3$ material nor Gilde et al.'s $TiB_2$—$Al_2O_3$ material appears to hold extensive promise for armor applications.

The present invention provides a novel method of making a two-phase ceramic composite shaped body composed of chromium diboride ($CrB_2$) and aluminum oxide ($Al_2O_3$). The present invention's methodology for making a $CrB_2$—$Al_2O_3$ composite body is unique particularly in that it is based on pressureless sintering. The present inventors have discovered that some two-phase composite compositions of chromium diboride and aluminum oxide—especially those that contain as much or more aluminum oxide than chromium diboride—can be prepared according to a process that includes pressureless sintering.

Like the two-phase ceramic composite of Talmy et al., the present invention's two-phase ceramic composite has a chromium diboride phase and an aluminum oxide phase. The present invention's chromium diboride-aluminum oxide system, Talmy et al's chromium diboride-aluminum oxide system, and Gilde et al.'s titanium diboride—aluminum oxide system are analogous insofar as each represents a ceramic-ceramic composite—i.e., a completely ceramic composite material composition constituted by two different "pure" ceramic material phases.

Generally speaking, pressureless sintering is a less expensive processing methodology than pressure-assisted sintering. Complex shapes can be prepared via pressureless sintering. However, complex shapes cannot be prepared via pressure-assisted sintering, because the application of pressure during sintering is counterproductive to the achievement of a desired complex shape. On the other hand, pressure assistance in the sintering process is necessary to prepare the vast majority of advanced ceramics, since the requisite densifications will not take place in the absence of pressure assistance. The present invention succeeds, without pressure assistance in the sintering process, in preparing complexly shaped ceramic articles having advanced capabilities such as involving hardness and/or toughness.

Other objects, advantages and features of the present invention will become apparent from the following detailed description of the present invention.

DESCRIPTION OF EXEMPLARY EMBODIMENTS OF THE INVENTION

According to the present invention's typical methodology for making a $CrB_2$—$Al_2O_3$ two-phase ceramic composite article, aluminum oxide and chromium diboride powders are intimately mixed in proportions to yield the desired volume percent ratio, based on the densities of the two species. The volumetric proportions will usually fall within the range between about 0% $CrB_2$-100% $Al_2O_3$ and about 50% $CrB_2$-50% $Al_2O_3$. Frequent inventive practice provides for volumetric proportions falling within the range between about 20% $CrB_2$-80% $Al_2O_3$ and about 30% $CrB_2$-70% $Al_2O_3$.

Optionally, the mixture (blend) of powders can then be milled to achieve smaller particle sizes. Additionally or alternatively, either or both of the $CrB_2$ powder and the $Al_2O_3$ powder can be milled prior to mixing, for similar purpose. In terms of "sinterability" of particulate, finer is generally better.

A "green ceramic" specimen is then prepared from the mixture using a known shaping technique. Any of several known shaping techniques may be applied to the $CrB_2$—$Al_2O_3$ mixture so as to render the $CrB_2$—$Al_2O_3$ mixture a $CrB_2$—$Al_2O_3$ green body. Conventional shaping techniques suitable for inventive practice include die pressing, cold isostatic pressing (OP), extrusion, slip casting, and injection molding. Cold isostatic pressing may be a preferred shaping technique for many inventive embodiments, because cold isostatic pressing tends to yield a higher "green density" as compared with other known shaping techniques. Generally speaking, the higher is the density of the green body, the easier is the sintering.

The green specimen is then fired in a non-oxidizing atmosphere to a temperature ranging from about 1600° C. to about 2050° C. The non-oxidizing atmosphere can be a vacuum, or an inert gas (e.g., argon), or a reducing gas. The 2050° C. temperature, which represents the upper limit of the firing temperature range, is near the melting point of aluminum oxide, which is 2054° C. In inventive practice, the specific firing temperature will vary with the particular $CrB_2$ and $Al_2O_3$ powders used, their volumetric proportions, and the firing atmosphere. Typically, the pressureless sintered ceramic body will be permitted to remain and cool in the furnace for a period of time after heating has concluded. This may be accomplished, for instance, by simply turning the furnace off, or alternatively, by programming the specific cooling rate.

Machining of ceramic entities is commonplace in the ceramics industry. The skilled artisan reading the instant disclosure will appreciate how machining may be effected for shape refinement of inventive ceramic entities. If necessary or appropriate, "green machining" of the present invention's green ceramic body, and/or "final machining" of the present invention's pressureless sintered ceramic body, may be implemented.

In testing their invention, the present inventors prepared a mixture of 20 volume-% $CrB_2$ and 80 volume-% $Al_2O_3$. The mixture was cold isostatic pressed to form a specifically shaped green body. The green body was fired in helium (He) at 1800° C., yielding a fully dense ceramic with flexural strength of 220 MPa.

According to usual inventive practice, the $Al_2O_3$ constituent represents at least about fifty percent of the overall volume of the inventive $CrB_2$—$Al_2O_3$ two-phase composite body, and hence the $CrB_2$ constituent represents no more than about fifty percent of the overall volume of the inventive $CrB_2$—$Al_2O_3$ two-phase composite body. Inventive green body embodiments having higher chromium diboride contents generally require higher firing temperatures, but should result in densified ceramic material that is stronger, tougher and harder, e.g., with better ballistic properties. Chromium diboride content from about twenty percent to about thirty percent is believed by the present inventors to be the optimum range for inventive practice, in order to achieve the best combinations of processing and properties.

Ballistic armor is a notable realm of inventive application. The present invention provides a methodology for cost-effectively producing complexly shaped bodies composed of an advanced ceramic material system that has been demonstrated in testing to be formidable when subjected to great force/energy such as associated with projectile impact. For instance, complexly shaped articles useful for ballistic personal/personnel armor protection, such as helmets and curved body-armor plates, can be propitiously manufactured using the inventive methodology.

Inventive practice is a viable option for diverse applications, including but not limited to ballistic armor applications. The present inventors' novel discovery that $CrB_2$—$Al_2O_3$ materials can be densified without being pressured expands the possibilities of armor applications and other applications. The present invention's pressureless sintered $CrB_2$—$Al_2O_3$ two-phase ceramic composite materials promise increased availability (e.g., larger-scale production) because of reduced costs and increased article-shaping capability/versatility. The potential of the inventive $CrB_2$—$Al_2O_3$ composites exceeds that of many ceramic materials manufactured via pressure-assisted sintering.

The present invention, which is disclosed herein, is not to be limited by the embodiments described or illustrated herein, which are given by way of example and not of limitation. Other embodiments of the present invention will be apparent to those skilled in the art from a consideration of the instant disclosure or from practice of the present invention. Various omissions, modifications and changes to the principles disclosed herein may be made by one skilled in the art without departing from the true scope and spirit of the present invention, which is indicated by the following claims.

What is claimed is:

1. A method for making a chromium diborid-aluminum oxide two-phase ceramic composite body, the method comprising:
    mixing chromium diboride powder and aluminum oxide powder to produce a mixture, said mixture consisting of said chromium diboride and said aluminum oxide, wherein said chromium diboride constitutes a percentage by volume of said mixture in the range between 21% and 30%, and said aluminum oxide constitutes a percentage by volume of said mixture in the range between 70% and 79%;
    shaping said mixture to form a green body, said green body including said chromium diboride and said aluminum oxide;
    pressureless sintering said green body in a non-oxidizing atmosphere at a firing temperature in the range between 1600° C. and 1699° C., the pressureless sintered said green body including said chromium diboride and said aluminum oxide;
    wherein said pressureless sintering of said green body is performed to obtain a chromium diboride-aluminum oxide two-phase ceramic composite that is fully dense.

2. The method of claim 1 wherein the method further comprises milling said mixture prior to said shaping.

3. The method of claim 1 wherein said non-oxidizing atmosphere is one of a vacuum, an inert gas, and a reducing gas.

4. The method of claim 1 wherein said shaping includes using at least one shaping technique selected from the group consisting of die pressing, cold isostatic pressing, extrusion, slip casting, and injection molding.

5. The method of claim 1 wherein the method further comprises cooling the pressureless sintered said green body.

6. The method of claim 5 wherein the method further comprises at least one of:
    machining said green body prior to said pressureless sintering; and
    machining the cooled pressureless sintered said green body.

7. The method of claim 1 wherein said chromium diboride constitutes a percentage by volume of said mixture in the range between 22% and 30%, and said aluminum oxide constitutes a percentage by volume of said mixture in the range between 70% and 78%.

8. The method of claim 1 wherein said chromium diboride constitutes a percentage by volume of said mixture in the range between 23% and 30%, and said aluminum oxide constitutes a percentage by volume of said mixture in the range between 70% and 77%.

9. A method for making a $CrB_2$—$Al_2O_3$ two-phase ceramic composite article, the method comprising:
preparing a blend of chromium diboride powder and aluminum oxide powder, said blend consisting of said chromium diboride and said aluminum oxide,
wherein the prepared said blend of chromium diboride powder and aluminum oxide powder is in volumetric proportions in the range between 21% $CrB_2$-79% $Al_2O_3$ and 30% $CrB_2$-70% $Al_2O_3$;
shaping said blend into a green body, said green body including said chromium diboride and said aluminum oxide;
densifying said green body in the absence of applied pressure in a non-oxidizing atmosphere, said densifying of said green body including heating said green body in a furnace to a temperature in the range between 1600° C. and 1699° C., the densified said green body including said chromium diboride and said aluminum oxide;
wherein said densifying of said green body is performed to obtain a chromium diboride-aluminum oxide two-phase ceramic composite that is fully dense.

10. The method of claim 9 wherein said shaping of said blend includes cold isostatic pressing.

11. The method of claim 9 wherein said non-oxidizing atmosphere is either a vacuous atmosphere or a gaseous atmosphere.

12. The method of claim 11 wherein said gaseous atmosphere is either an inert gaseous atmosphere or a reducing gaseous atmosphere.

13. The method of claim 9 wherein the method further comprises at least one of:
machining said green body prior to said densifying of said green body; and
machining the densified said green body.

14. The method of claim 9 wherein the prepared said blend of chromium diboride powder and aluminum oxide powder is in volumetric proportions in the range between 22% $CrB_2$-78% $Al_2O_3$ and 30% $CrB_2$-70% $Al_2O_3$.

15. The method of claim 9 wherein the prepared said blend of chromium diboride powder and aluminum oxide powder is in volumetric proportions in the range between 23% $CrB_2$-77% $Al_2O_3$ and 30% $CrB_2$-70% $Al_2O_3$.

* * * * *